US00PP29681P3

(12) United States Plant Patent
Hansen

(10) Patent No.: US PP29,681 P3
(45) Date of Patent: Sep. 18, 2018

(54) *VERONICA* PLANT NAMED 'PINK POTION'

(50) Latin Name: ***Veronica* hybrid**
Varietal Denomination: Pink Potion

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 30 days.

(21) Appl. No.: 15/330,912

(22) Filed: Nov. 14, 2016

(65) Prior Publication Data

US 2018/0139880 P1 May 17, 2018

(51) Int. Cl.
*A01H 5/02* (2018.01)

(52) U.S. Cl.
USPC ..... Plt./251
CPC ..... *A01H 5/02* (2013.01)

(58) Field of Classification Search
USPC ..... Plt./251
CPC ..... A01H 5/02; A01H 5/00; A01H 6/68
See application file for complete search history.

(56) References Cited

U.S. PATENT DOCUMENTS

PP16,182 P3 * 1/2006 Farrow ..... A01H 5/02 Plt./251
PP16,311 P2 * 3/2006 Verschoor ..... A01H 5/02 Plt./251
PP18,743 P2 * 4/2008 Oudshoorn ..... A01H 5/02 Plt./251
PP23,938 P2 * 10/2013 Verschoor ..... A01H 5/02 Plt./251
PP24,756 P2 * 8/2014 Verschoor ..... A01H 5/02 Plt./251
PP24,785 P2 * 8/2014 Verschoor ..... A01H 5/02 Plt./251
PP26,416 P3 * 2/2016 Korlipara ..... A01H 5/02 Plt./251
PP27,084 P2 * 8/2016 Oudolf ..... A01H 5/02 Plt./251
PP27,257 P2 * 10/2016 van den Hoogen ..... A01H 5/02 Plt./251

OTHER PUBLICATIONS

Michell's Walters Gardens, Inc. 2015-16 Availability List, Jan. 4, 2016 retrieved on Oct. 26, 2017, retrieved from the Internet at http://www.michells.com/availabilities/Waltersavailability.pdf, pp. 1 and 28 (Year: 2016).*

* cited by examiner

*Primary Examiner* — June Hwu

(57) ABSTRACT

The new and distinct cultivar of hybrid ornamental spiked speedwell plant *Veronica* 'Pink Potion' with dense flower production of numerous self-cleaning pink flowers covering long, deep green foliage beginning in mid-summer and continuing until mid-fall when deadheaded. 'Pink Potion' is suitable for a potted plant, for the garden, and for cut flower arrangements.

1 Drawing Sheet

Botanical classification: *Veronica* hybrid.
Variety denomination: 'Pink Potion'.

BACKGROUND OF THE INVENTION

The present invention relates to the new and distinct cultivar of spiked speedwell, botanically known as *Veronica* hybrid, and hereinafter also referred to by the cultivar name 'Pink Potion' or "the new plant". The new plant selected as a single seedling among a cross performed under direction of the inventor at a wholesale perennial nursery in Zeeland, Mich. of a proprietary unreleased seedling of 'Purpleicious' U.S. Plant Pat. No. 17,639 known by the breeder code 08-57-03 (not patented) times *Veronica* 'Rotfuchs' (not patented) (more commonly sold in the U.S. under the name 'Red Fox') on Jun. 29, 2012. The new plant was grown on in trials at the same nursery in Zeeland, Mich. and when passed the initial evaluation in early summer of 2013 was assigned the breeder code 12-31-01. The plant has been asexually propagated by basal shoot tip cuttings in the greenhouses at the same nursery in Zeeland, Mich., with subsequent asexually propagated plants found to be stable and identical to the original selection with all the same traits as the original seedling.

BRIEF SUMMARY OF THE PLANT

*Veronica* 'Pink Potion' is unique from all other spiked speedwell known to the inventor. Several other cultivars have blue to purple flowers, but this is the only variety known by the applicant to have the following trait combinations.

Compared to the female parent, 08-57-03, the new plant has flowers that are pink colored rather than purple and is shorter. Compared to the male parent 'Rotfuchs' the new plant has flowers of a pink rather than a deep fuchsia pink, is slightly taller and has more heavily-branched scapes.

The closest comparison varieties known to the inventor in flower color are *Veronica* 'Tickled Pink' U.S. Plant Pat. No. 16,182 and *Veronica* 'Sweet Lullaby' U.S. Plant Pat. No. 23,611. The new plant has cleaner, less mildew prone foliage than 'Sweet Lullaby' and slightly different flower color.

Compared to 'Tickled Pink' the new plant is taller with slightly different pink flower color.

Table 1 below shows a more concise comparison of some of the other similar spike speedwell cultivars with height of plant including panicle and total flowers produced on single branched stem or inflorescence:

TABLE 1

VERONICA COMPARISONS

| Cultivar | RHS flower color | Panicle height | Flowers per inflo-rescence | leaf length | U.S. Plant Pat. No. |
|---|---|---|---|---|---|
| 'Pink Bomb' | 65A-65C | 55 cm | 1500 | 9.6 cm | PP24,756 |
| 'Verspink' | 63A-64B | 32.5 cm | 120 | 4.5 cm | PP24,785 |
| 'Tnvera' | 69A-69B | 27 cm | 70 | 3.5 cm | PP26,416 |
| 'Candied Candle' | 64B-64C | 51.3 cm | 360 | 9.7 cm | PP27,084 |
| 'Allchoice' | 65A-65B | 40.5 cm | 250 | 5.6 cm | PP27,257 |
| 'Atomic Silvery Pink Ray' | 62C-65B | 54.5 cm | 1400 | 8.1 cm | PP23,938 |
| 'Sweet LulLaby' | 62D-65D | 28 cm | 260 | 5.5 cm | PP23,611 |
| 'Pink Eveline' | 64A-64C | 38.5 cm | 100 | 4.0 cm | PP18,743 |
| 'Pink Panther' | 73A-73B | 56 cm | 400 | 8.6 cm | PP16,311 |
| 'Tickled Pink' | 68B | 13.5 cm | 140 | 13 cm | PP16,182 |
| 'Pink Potion' | 68C | 47 cm | 2500 | 7.0 cm | application |

The following are traits of *Veronica* 'Pink Potion' that in combination distinguish it from all other spiked speedwell known to the inventor:

1. Tall, well-branched scapes producing nearly continuous heavy flower show that covers the top of the plant.
2. Numerous self-cleaning flowers of pink petals beginning in mid-summer.
3. Lanceolate to oblanceolate foliage of deep green.

BRIEF DESCRIPTION OF THE DRAWINGS

The photographs of the new plant demonstrates the overall appearance and unique traits of 'Pink Potion' as a two-year old plant grown in a full-sun trial garden in Zeeland, Mich. with supplemental water and fertilizer provided as needed. The colors are as accurate as reasonably possible with color reproductions. Variation in ambient light spectrum, source and direction may cause the appearance of minor variation in color.

DETAILED BOTANICAL DESCRIPTION

Figure 1:
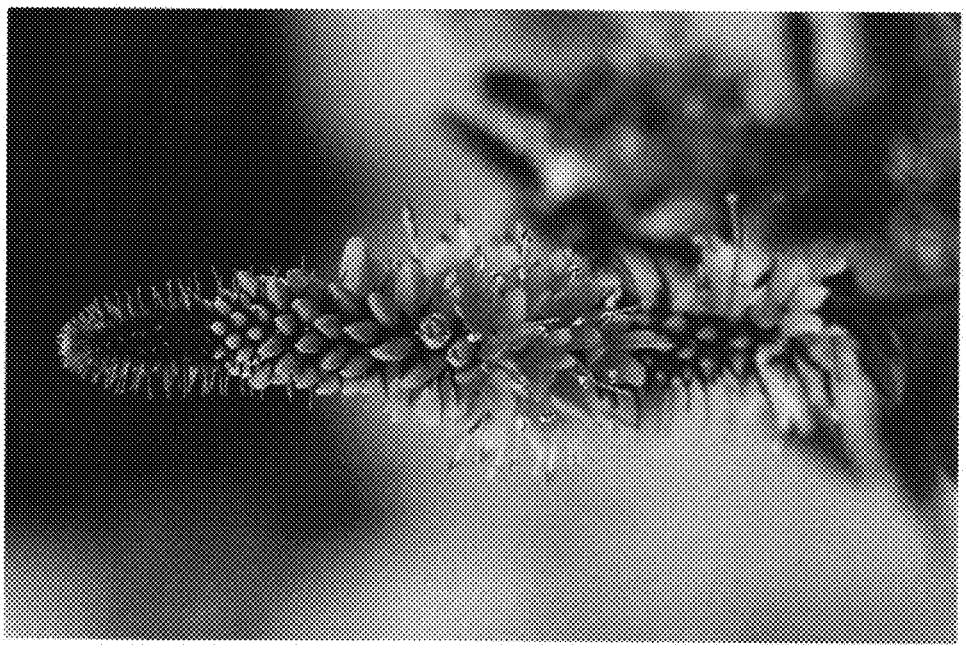
FIG. 1 shows a close-up of the scape with buds and flowers.
Figure 2:
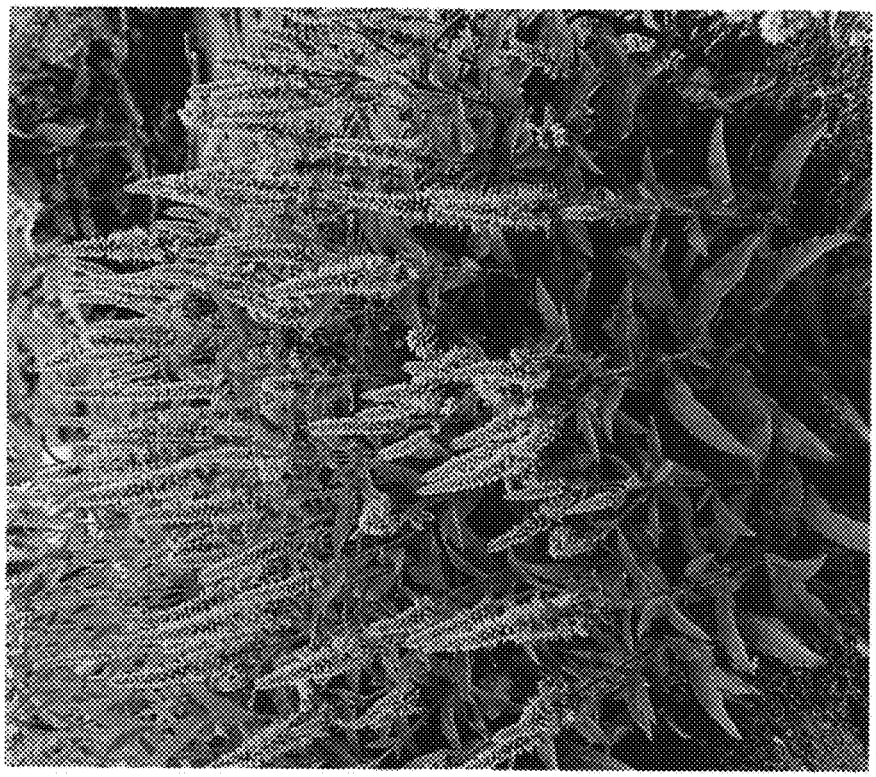
FIG. 2 shows the plant in the landscape in mid-summer.

The following descriptions and color references of 'Pink Potion' are based on the 2001 edition of The Royal Horticultural Society Colour Chart except where common dictionary terms are used. *Veronica* 'Pink Potion' has not been observed under all possible environments. The phenotype may vary slightly with different growing environments such as temperature, light, fertility, soil pH, moisture and maturity levels, but without any change in the genotype. The following observations and size descriptions are based on two-year old plants in the full-sun trial garden of a nursery in Zeeland, Mich. with supplemental fertilizer and water as needed.

Botanical classification: *Veronica* hybrid;

Parentage: Female (seed parent) proprietary unreleased breeding plant known only as 08-57-03; male (pollen parent) 'Rotfuchs';

Plant habit: Hardy herbaceous perennial, compact, with several stems, average about 47.0 cm tall in flower and about 88.0 cm wide; flowering beginning early July in Michigan and continuing for about 5 weeks with repeat if deadheaded through early fall;

Leaves: Simple, flat, lanceolate to oblanceolate, opposite, serrulate, acute apex, attenuate base; adaxial surface puberuleut, abaxial glabrous; to about 7.0 cm long by about 2.8 cm wide decreasing in both length and width distally;

Leaf color: Adaxial between RHS 137A and RHS 139A; abaxial nearest RHS 138A;

Veins: Pinnate; adaxial and abaxial midrib puberulent;

Vein color: Adaxial midrib nearest RHS 146D; abaxial midrib nearest RHS 145A; adaxial and abaxial secondary veins indistinguishable from surrounding leaf;

Petiole: Simple, slightly concavo-convex; adaxial puberulent, abaxial glabrous; about 2.5 cm long and about 3.0 mm wide;

Petiole color: Adaxial nearest RHS 144A; abaxial nearest RHS 144A;

Stem: About 30 per plant; terete; about 24.0 cm tall to top of foliage, and 47.0 cm tall to top of panicle; about 3.0 mm diameter at base; puberulent to glandular; color as expanding nearest RHS 146D and in maturity nearest RHS 146B developing undertone of nearest RHS N186B when exposed to high ultraviolet light;

Flower buds one day prior to opening: Convolute, narrowly ovoid, obtuse apex; about 5.5 mm long and 2.5 mm diameter;

Bud color: Nearest RHS 67C one to two days prior to opening; buds one week prior to opening between RHS 69B and RHS 69C proximally and nearest RHS 67D toward apex;

Flowers: Perfect, zygomorphic, campanulate; on heavily branched upright to spikes; numerous, congested, about 14 flowers per centimeter; approximately 580 per main spike and about 2500 to 3000 flowers per branched panicle; about 4.5 mm across, about 5.0 mm tall and about 6.0 mm deep; no detectible fragrance; flowers persist individually for 4 to 6 days whether on the plant or as cut flower; self-cleaning; outwardly and slightly upwardly;

Petals: Four; margins entire; apices acute; corolla tube fused in basal about 2.0 mm; upper petal about 6.0 mm long and about 4.5 mm across; lower petal about 6.0 mm long and about 2.5 mm across; two side petals about 6.0 mm long and about 3.5 mm across; glabrous outer and inner surfaces except pilosulose in basal adaxial 2.0 mm long fused tube with hair white, lighter than RHS 155D;

Petal color: Adaxial and abaxial surfaces nearest RHS 68C with basal 2.0 mm nearest RHS N155B of both adaxial and abaxial surfaces; prior to dehiscing distal 4.0 mm of adaxial and abaxial surfaces lighten to between RHS 68C and RHS 68D;

Androecium: Stamens two, exserted;

*Filaments*.—Two, base fused to proximal adaxial petal; about 6.5 mm by 0.3 mm; color between RHS 67C and RHS 67D.

*Anther*.—Oblong; dorsifixed, longitudinal, versatile; acute apex; about 2.2 mm by about 1.0 mm; color nearest RHS 71A.

*Pollen*.—Abundant, globose, less than 0.1 mm; color between RHS 11B and RHS 11C.

Gynoecium: Single; simple;

*Style*.—Single; straight, extending outward, perpendicular to flower face; persists after petals drop; about 5.0 mm long by about 0.2 mm diameter; color nearest RHS 72B.

*Stigma*.—Semi-spherical with rounded apex; about 0.8 mm in diameter; color nearest RHS N187D.

*Ovary*.—Spherical; about 0.7 mm in diameter; nearest RHS N144D.

Sepals; Four; entire, surface dull, ovate to narrowly ovate, acute apex, base fused forming corolla; abaxial sparsely pubescent with minute glandular hairs, adaxial glabrous; upper pair about 3.0 mm long and about 0.5 mm wide, lower pair about 4.0 mm long by about 0.5 mm wide; color abaxial and adaxial nearest RHS 137A;

Peduncle: About 30 per plant; heavily-branched panicle, strong, erect, terete; glandular to puberulent; about 40.0 cm long and about 3.0 mm in diameter at the base; two to four primary branches to about 35.0 cm long and 2.4 mm diameter with each primary branch typically with two secondary branches about 30 cm long and 2.0 mm diameter;

Peduncle color: Nearest RHS 146B;

Pedicel: Upright to outwardly; stiff, terete; puberulent about 0.5 mm long and 0.5 mm diameter;

Pedicel color: Nearest RHS 138B;

Bract: Single subtending each flower, linear, narrowly acute apex, entire, sessile, based fused to peduncle, proximal bracts about 1.0 cm long and about 2.0 mm wide and decreasing distally to about 3.0 mm long and less than about 0.5 mm wide;

Bract color: RHS 137A above and RHS 137C below;

Fruit: Emarginate, globose, two bi-valued loculicidal capsule; about 3.0 mm long and about 3.0 mm diameter; color on maturity between RHS N199A and RHS 199A;

Seed: Slightly flattened ellipsoid, about 0.8 mm long, 0.5 mm across and 0.2 mm thick; color between RHS 165A and RHS 166A;

Propagation: Stem and tip cuttings root in about 2 weeks and finish to flowering in a 3.8 liter container in 8 to 10 weeks following a vernalization period of about 8 weeks;

Hardiness, pest and disease resistance: The plant grows best with adequate moisture and drainage, but is able to tolerate some drought when mature. Hardiness at least from USDA zone 4 through 8. Disease and pest resistance beyond what is typical of that common to other spiked speedwell has not been observed.

I claim:

1. A new and distinct cultivar of ornamental spiked speedwell plant, *Veronica* 'Pink Potion', as herein described and illustrated.

* * * * *